United States Patent [19]

Rothgery et al.

[11] 4,143,044
[45] Mar. 6, 1979

[54] PROCESS FOR MAKING SELECTED 3-TRIHALOMETHYL-5-LOWER ALKOXY-1,2,4-THIADIAZOLES

[75] Inventors: Eugene F. Rothgery, North Branford; Hans Juergen A. Schroeder, Hamden, both of Conn.

[73] Assignee: Olin Corporation, New Haven, Conn.

[21] Appl. No.: 893,550

[22] Filed: Apr. 5, 1978

[51] Int. Cl.² .................................. C07D 285/08
[52] U.S. Cl. .................................. 260/302 D
[58] Field of Search .......................... 260/302 D

[56] References Cited

U.S. PATENT DOCUMENTS

| 3,260,588 | 7/1966 | Schroeder | 260/302 D |
|---|---|---|---|
| 3,260,725 | 7/1966 | Schroeder | 260/302 D |
| 3,428,681 | 2/1969 | Kippur et al. | 260/302 D |
| 3,822,280 | 7/1974 | Meser et al. | 260/306.8 D |
| 3,890,338 | 6/1975 | Wojtowicz et al. | 260/302 D |
| 3,890,339 | 6/1975 | Gavin | 260/302 D |

FOREIGN PATENT DOCUMENTS 261605  5/1968  Austria .................................. 260/302 D

OTHER PUBLICATIONS

Goerdeler, Ber. Deut. Chem., vol. 87, pp. 57-67 (1954).

Primary Examiner—Alton D. Rollins
Attorney, Agent, or Firm—William A. Simons; Thomas P. O'Day

[57] ABSTRACT

A process for producing selected 3-trihalomethyl-5-lower alkoxy-1,2,4-thiadiazole compounds by the reaction of N-halotrihaloacetamidines with alkali metal xanthate salts.

10 Claims, No Drawings

PROCESS FOR MAKING SELECTED 3-TRIHALOMETHYL-5-LOWER ALKOXY-1,2,4-THIADIAZOLES

BACKGROUND OF THE INVENTION

1. Field of the Invention

This invention relates to a process for making selected 3-trihalomethyl-5-lower alkoxy-1,2,4-thiadiazole compounds.

2. Description of the Prior Art

3-Trichloromethyl-5-lower alkoxy-1,2,4-thiadiazole compounds are known as effective soil fungicides. See U.S. Pat. Nos. 3,260,588 and 3,260,725, both of which were issued to H. A. Schroeder on July 17, 1966. As noted in these Schroeder patents, 3-trichloromethyl-5-lower alkoxy-1,2,4-thiadiazole compounds have been prepared by first reacting trichloroacetamidine or its hydrochloride with trichloromethane sulfenyl chloride in the presence of alkali to form 3-trichloromethyl-5-chloro-1,2,4-thiadiazole. This 5-chloro compound is then reacted with alkali metal in the excess of lower alcohol. Also see U.S. Pat. Nos. 3,890,338 and 3,890,339, which issued to Wojtowicz et al. and Gavin, respectively, on June 17, 1975.

While this reaction route for making 3-trichloromethyl-5-lower alkoxy-1,2,4-thiadiazole compounds has certain characteristics which make it commercially desirable, the present invention presents a new and simple alternate route for producing these compounds without making the 3-trichloromethyl-5-chloro-1,2,4-thiadiazole intermediate. Ring closure directly produces the desired 5-lower alkoxy compounds.

BRIEF SUMMARY OF THE INVENTION

The present invention comprises a method for making selected 3-trihalomethyl-5-lower alkoxy-1,2,4-thiadiazole compounds by reacting the corresponding N-halotrihaloacetamidine with the corresponding alkali metal xanthate salt.

DETAILED DESCRIPTION

The production of selected 3-trihalomethyl-5-lower alkoxy-1,2,4-thiadiazole compounds by the process of the present invention is illustrated by the following equation:

$$CX'_3-\underset{NH_2}{\underset{|}{C}}=NX'' + M-S-\underset{S}{\overset{\|}{C}}-O-R \xrightarrow{-H_2S, -MX''}$$

$$CX'_3-\underset{N\diagdown_S\diagup}{\overset{C \rlap{\phantom{X}}}{\|}}\overset{N}{\underset{\|}{\phantom{X}}} C-OR$$

wherein
X' is Cl or F;
X" is Cl, Br or I;
M is sodium or potassium; and
R is a lower alkyl group having from 1 to 4 carbon atoms.

In the preferred embodiment of the present invention, sodium or potassium ethyl xanthate is reacted with N-chloro- or N-bromotrichloroacetamidine to produce 3-trichloromethyl-5-ethoxy-1,2,4-thiadiazole, which has been found to be a broad-spectrum, commercially acceptable fungicide.

These N-halotrihaloacetamidine reactants can be conveniently prepared by the selective halogenation of the corresponding trihaloacetamidine compound. See U.S. Pat. No. 3,428,681, which issued to Kippur and Bailey on Feb. 18, 1969.

The alkali metal xanthate salts may be easily made by reacting the corresponding alkali metal hydroxide and lower alcohol with $CS_2$. See Rau, S.R., *Xanthates and Related Compounds*, Marcel Dekkler, New York (1971).

The molar ratio of the two reactants is not critical to the present invention and any suitable ratio may be employed. Usually, it is desirable to avoid a large molar excess of the N-halotrihaloacetamidine compounds since these are oxidizing agents and, in excess, their presence may cause decomposition of the desired product. Preferably, the molar ratio of the N-halotrihaloacetamidine to the xanthate salt may be in the range of from about 1.25:1.0 to about 1.0:1.5. More preferably, this ratio is in the range of from about 1.0:1.0 to about 1.0:1.1 in order to avoid a waste of excess reactant.

The reaction of the present invention may be preferably carried out in the presence of a suitable organic solvent or the mixture of an organic solvent and water. Suitable organic solvents include acetonitrile, tetrahydrofuran, or methylene chloride. The latter solvent when combined with water is most preferred because of its relative ease of handling and its lesser possibility of causing toxicity problems than most other commercially available solvents. The molar ratio of the solvent to the reactants is not critical to the present invention and any suitable amount of solvent or solvents may be employed.

Other reaction parameters such as reaction temperatures, pressures, and times are generally not critical limitations of the present invention and this invention is not to be limited thereby. Any suitable reaction temperatures may be employed that result in a commercially acceptable yield. Preferably, reaction temperatures in the range from about 0° C. to about 50° C., more preferably from about 5° C. to about 30° C., may be utilized. Likewise, any suitable reaction pressure may be employed. Atmospheric pressure is most preferred because it does not require any special apparatus. Further, the reaction time for the present reaction normally is substantially instantaneous; however, the combining of the reactants together in the reaction vessel is normally allowed to precede very slowly to prevent uncontrolled exothermic flashing from occurring. Normally, from about 0.5 to about 3 hours addition time for each reaction is suitable.

After the completion of the reaction the product may be recovered by any conventional method such as extraction, distillation, solvent-stripping, filtration, and crystallization procedures. In particular, one method is to extract the desired product from the reaction mixture with a hydrocarbon, such as petroleum ether, then distilling this extracted product to remove low boiling impurities and the like. The recovered product may be then used as a fungicide as is or may be mixed into any conventional fungicidal formulation.

The present invention is further illustrated by the following examples. All percentages and proportions are by weight unless otherwise explicitly indicated.

EXAMPLE 1

20 g (0.1 mole) of N-chlorotrichloroacetamidine and 16 g (0.1 mole) of potassium ethyl xanthate were mixed in 300 ml of tetrahydrofuran. A spontaneous exothermic reaction occurred requiring ice cooling. After stirring the mixture overnight, the resulting solids were filtered off, the solvent removed by a vacuum and the remaining product distilled at 95° C. under a vacuum of 10.5mm; obtained was 10 g of material containing 85% by weight 3-trichloromethyl-5-ethoxy-1,2,4-thiadiazole.

EXAMPLE 2

32 g (0.2 mole) of potassium ethyl xanthate was dissolved in 175 ml of water. This was stirred rapidly while a solution of 48 g (0.2 mole) of N-bromotrichloroacetamidine in 150 ml of methylene chloride was added over 15 minutes. Then, the mixture was stirred one hour at room temperature. The dark methylene chloride layer was separated and the water layer extracted with 100 ml of methylene chloride. The combined methylene chloride fractions were dried over magnesium sulfate and filtered. Next, the solvent was evaporated and then the crude product was distilled at 75° C. under a vacuum of 0.9mm to give 26 g of 3-trichloromethyl-5-ethoxy-1,2,4-thiadiazole.

EXAMPLE 3

17.6 g (0.11 mole) of potassium ethyl xanthate was dissolved in 300 ml of acetonitrile. The solution was cooled to 5° C. and an acetonitrile solution of 20 g (0.1 mole) of N-bromotrifluoroacetamidine dropped in over 45 minutes. The reaction was maintained below 10° C. with ice. The mixture was stirred one hour at room temperature and then filtered. The solvent was removed under vacuum and the resulting crude product distilled at 85°-90° C./35 mm to give 11 g of product with an assay of 45% 3-trifluoromethyl-5-ethoxy-1,2,4-thiadiazole.

What is claimed is:

1. A process for producing selected 3-trihalomethyl-5-lower alkoxy-1,2,4-thiadiazoles wherein said trihalomethyl group is selected from the group consisting of $CCl_3$ and $CF_3$ and said lower alkoxy group is selected from an alkoxy group having from 1 to 4 carbon atoms comprising reacting the corresponding N-halotrihaloacetamidine compound, wherein said N-halo group is selected from the group consisting of Cl, Br and I, with the corresponding alkali metal lower alkyl xanthate salt, wherein said alkali metal is selected from the group consisting of sodium and potassium.

2. The process of claim 1 wherein said trihalomethyl group is $CCl_3$.

3. The process of claim 1 wherein said lower alkoxy group is ethoxy.

4. The process of claim 1 wherein the molar ratio of said N-halotrihaloacetamidine to said alkali metal xanthate salt is in the range of from about 1.25:1.0 to about 1.0:1.5.

5. The process of claim 4 wherein the reaction is carried out in the presence of an organic solvent selected from the group consisting of acetonitrile, tetrahydrofuran, and a mixture of methylene chloride and water.

6. The process of claim 5 wherein said reaction temperature is in the range of from about 0° C. to about 50° C.

7. The process of claim 6 wherein said N-halo group is selected from the group consisting of Cl and Br.

8. The process of claim 7 wherein said trihalomethyl group is $CCl_3$.

9. The process of claim 8 wherein said lower alkoxy group is ethoxy.

10. The process of claim 9 wherein said molar ratio of the reactants is in the range of about 1.0:1.0 to about 1.0:1.1; the reaction is carried out in the presence of solvent selected from the group of methylene chloride and a mixture of methylene chloride and water; and said reaction temperature is in the range of from about 5° C. to about 30° C.

* * * * *